United States Patent [19]

Ogawa

[11] Patent Number: 5,337,017
[45] Date of Patent: Aug. 9, 1994

[54] APPARATUS FOR DETECTING ALCOHOL CONTENT OF LIQUID

[75] Inventor: Kenji Ogawa, Himeji, Japan

[73] Assignee: Mitsubishi Denki Kabushiki Kaisha, Tokyo, Japan

[21] Appl. No.: 96,270

[22] Filed: Jul. 26, 1993

[30] Foreign Application Priority Data

Aug. 11, 1992 [JP] Japan .................................. 4-214138

[51] Int. Cl.$^5$ ...................... G01N 27/22; G01N 33/22
[52] U.S. Cl. ................................... 324/682; 73/61.43
[58] Field of Search ............... 73/61.45, 61.44, 61.43; 324/682, 677, 675, 668

[56] References Cited

U.S. PATENT DOCUMENTS

| | | | |
|---|---|---|---|
| 5,005,402 | 4/1991 | Pischinger et al. | 73/61.43 X |
| 5,091,704 | 2/1992 | Kopera | 324/682 X |
| 5,182,523 | 1/1993 | Ertel et al. | 73/61.43 X |
| 5,196,801 | 3/1993 | Nogami et al. | 73/61.43 X |
| 5,231,358 | 7/1993 | Kapsokavathis et al. | 73/61.43 X |
| 5,261,270 | 11/1993 | Gonze et al. | 73/61.43 |

FOREIGN PATENT DOCUMENTS 0499841  8/1992  European Pat. Off. ............ 324/682

*Primary Examiner*—Thomas P. Noland
*Assistant Examiner*—Joseph W. Roskos
*Attorney, Agent, or Firm*—Sughrue, Mion, Zinn, Macpeak & Seas

[57] ABSTRACT

An apparatus for detecting an alcohol content of a liquid with high accuracy regardless of variance in a resonance frequency of a parallel resonance circuit constituted by inductance of a coil, capacity presented by a fluid within a liquid passage of a sensor unit and others. High-frequency voltage signals appearing at both ends of a resistor of a detector circuit connected in series to the coil are compared in respect to phase by a phase comparator, wherein difference signal resulting from the comparison is supplied to a voltage-controlled oscillator through a comparison integrator, the oscillation signal $S_{vco}$ of the oscillator being supplied to one end of the resistor through an amplifier. Through this phase synchronization loop, the oscillation frequency of the oscillator is forced to coincide with the resonance frequency, whereby a signal $S_{out}$ having a frequency bearing one-to-one correspondence to the resonance frequency is obtained from a frequency divider. By providing a frequency division ratio adjusting circuit for adjusting a frequency division ratio of the frequency divider, alcohol content can be detected with high frequency regardless of apparatus-dependent variance in the resonance frequency.

4 Claims, 5 Drawing Sheets

APPARATUS FOR DETECTING ALCOHOL CONTENT OF LIQUID

BACKGROUND OF THE INVENTION

1. Field of the Invention

The present invention relates to an alcohol content detecting apparatus for detecting or measuring a content of alcohol such as methanol of an alcohol-admixed liquid such as a liquid fuel for an internal combustion engine of a motor vehicle or the like.

2. Description of the Related Art

In recent years, a mixture of gasoline with methanol tends to be increasingly used as a fuel for internal combustion engines (hereinafter also referred to simply as the engine) of motor vehicles in U.S.A and European countries among others with a view to saving petroleum resources and reducing the air pollution ascribable to the exhaust gas of the motor vehicles.

When such methanol-admixed fuel is used as it is in the engine which is designed to operate with a gasoline fuel, the air-fuel mixture becomes lean, making it difficult or impossible to operate the engine, because the methanol-admixed fuel has a smaller theoretical air-fuel ratio when compared with the gasoline fuel. Under the circumstances, it is generally practiced to detect the content of methanol in the methanol-admixed fuel to thereby regulate correspondingly the air-fuel ratio, the ignition timing or other control quantities for the engine operation.

In conjunction with the detection of the methanol content of the fuel, there has heretofore been proposed a method which is based on detection of a dielectric constant of the methanol-admixed fuel and a method based on detection of a refractive index of the fuel. The applicant has already proposed an apparatus for detecting the methanol content on the basis of detection of the dielectric constant of the fuel (refer to Japanese Patent Application No. 22488/1991). For a better understanding of the background techniques of the present invention, this apparatus will be described by reference to FIG. 6.

Referring to the figure, the methanol content detecting apparatus includes a sensor unit denoted generally by A which is comprised of a cylindrical insulation tube 1 formed of an insulation material such ceramic, an oil-resistive plastic material and having an inner cavity or space in which a fuel passage is defined, as mentioned below. Disposed within the inner space 2 is a cylindrical electrode 3 having a cylindrical outer surface extending substantially in parallel with an inner cylindrical wall surface of the insulation tube 1 and disposed coaxially with the latter. A coil of a single layer winding 4 is provided as wound around the outer surface of the insulation tube 1 in opposition to the electrode 3. A fuel passage 2 is defined between the outer peripheral surface of the electrode 3 and the inner periphery of the coil 4 with the wall of the insulation tube 1 being interposed therebetween.

The electrode 3 is mounted to a flange 5 which in turn is coupled fluid-tightly to the insulation tube 1 with a fuel seal 7 interposed therebetween, whereby a fuel container, so to say, is realized as a whole. In the case of the illustrated example, the flange 5 is formed integrally with the electrode 3. Nipples 6 are provided for introducing the fuel into the fuel container of the sensor unit A.

A detection circuit for processing the output signal generated by the sensor unit A is generally denoted by a reference symbol B. The single-layer-winding coil 4 has a lead wire 4a connected to one end of a resistor 10 which constitutes a part of the detection circuit B and the other lead wire 4b which is grounded.

Signals appearing at opposite ends of the resistor 10 are supplied to a phase comparator 11 to be compared with each other. The output signal of the phase comparator 11 is supplied to a comparison integrator 13 through a low-pass filter 12. The integrator 13 is additionally supplied with a reference voltage $V_{ref}$ corresponding to a phase difference of 0°. A difference between the output signal of the filter 12 and the reference voltage $V_{ref}$ is integrated by the comparison integrator 13, the output of which is supplied to a voltage-controlled oscillator 14 as a control signal therefor. An oscillation signal $S_{vco}$ of a high frequency outputted from the voltage-controlled oscillator 14 is applied to the other end of the resistor 10 via an output amplifier 15. Further, the oscillation signal $S_{vco}$ outputted from the voltage-controlled oscillator 14 is supplied to a frequency divider 16.

Next, operation of this methanol content detection apparatus will be described.

FIG. 7 shows an equivalent circuit of the sensor unit A. In the figure, L represents an inductance of the single-layer winding coil 4, $C_f$ represents a capacity which is effective between the coil 4 and the electrode 3. This capacity $C_f$ will vary in dependence on a dielectric constant $\epsilon$ of a fuel flowing through the fuel passage 2. Further, $C_s$ represents a capacity provided by the insulation material forming the tube 1 which serves to protect the single-layer-winding coil 4 from the fuel, and $C_p$ generally represents stray capacitance parasitic to the lead wire 4a, input capacitance of the phase comparator 11 and so forth which are insusceptible to the influence of the dielectric constant $\epsilon$ of the fuel.

When the frequency of a voltage signal applied to the lead wire 4a of the sensor unit A is varied, the sensor unit A exhibits a parallel LC-resonance characteristic, wherein a parallel resonance frequency f can approximately be given by the following expression:

$$f = 1/[2\pi\{L(C_p + 1/(1/C_s + 1/C_f))\}[ = k/(a + b \times \epsilon) \quad (1)$$

where k, a and b represent constants determined by structural and geometrical factors of the sensor unit A such as the diameter and thickness of the insulation tube 1, the dielectric constant of the insulation material of the tube 1, distance between the electrode 3 and the single-layer-winding coil 4, self-inductance thereof and so forth.

As can be seen from the expression (1), the resonance frequency f depends on the dielectric constant $\epsilon$ of the fuel. Consequently, as the dielectric constant $\epsilon$ of the fuel increases, the resonance frequency f becomes lower. In the experimental measurement of methanol content of a fuel mixture of methanol and gasoline conducted by the inventors, the resonance frequency f exhibited a change illustrated in FIG. 8 as a function of the content of methanol. Thus, by detecting a signal corresponding to the resonance frequency f, it is possible to detect the dielectric constant $\epsilon$ of the fuel and hence the methanol content of the methanol-admixed fuel.

The detection circuit B is so configured as to detect the resonance frequency f mentioned above. More specifically, when the oscillation signal $S_{vco}$ is applied to the other end of the resistor 10 from the voltage-controlled oscillator 14 through the amplifier 15 in the state in which a methanol-admixed fuel is flowing through the fuel passage 2, there are obtained high-frequency voltage signals at both ends, respectively, of the resistor 10 (one from the coil 4 and the other from the series circuit of the resistor 10 and the single-layer-winding coil 4). These two high-frequency voltage signals are supplied to the phase comparator 11 for phase comparison.

In this case, when the frequency of the oscillation signal $S_{vco}$ outputted from the voltage-controlled oscillator 14 is equal to the resonance frequency f mentioned above, the current is in phase with the voltage, resulting in that the difference in phase between the two high-frequency voltage signals appearing at both ends of the resistor 10, respectively, becomes zero. Consequently, a signal corresponding to the phase difference of zero is outputted from the phase comparator 11 and thus from comparison integrator 13, whereby the oscillation frequency of the voltage-controlled oscillator 14 is held constant as it is.

In contrast, when the frequency of the oscillation signal $S_{vco}$ outputted from the voltage-controlled oscillator 14 is deviated from the resonance frequency f of the sensor unit A, the current will then be out of phase with the voltage, as a result of which the difference in phase between the two high-frequency voltage signals appearing at both ends of the resistor 10 assumes a value not equal to zero. Consequently, a signal corresponding to the phase difference is outputted from the phase comparator 11 and hence from the comparison integrator 13, whereby the voltage-controlled oscillator 14 is so controlled that the oscillation frequency thereof becomes equal to the resonance frequency f and that the phase difference between the two high-frequency voltage signals mentioned above becomes zero degree.

In this manner, the voltage-controlled oscillator 14 is controlled so that the oscillation frequency thereof remains constantly equal to the resonance frequency f, whereby an output signal $S_{out}$ of a frequency bearing one-to-one correspondence to the resonance frequency f is obtained from the frequency divider 16.

The hitherto known methanol content detection apparatus of the structure described above however suffers from a problem that because thickness of the insulation tube 1 as well as distance between the insulation tube 1 and the electrode 3 and hence the parasitic capacitance are inevitably susceptible to variance from one to another apparatus, incurring corresponding change in the resonance frequency f and hence in the frequency $f_{out}$ of the output signal $S_{out}$ in dependence on the apparatuses as used even for a same methanol content (refer to FIG. 8), whereby difficulty is encountered in detecting accurately the methanol content of the methanol-admixed fuel without any appreciable influence of the apparatus-dependent variance.

SUMMARY OF THE INVENTION

In the light of the state of the art, it is an object of the present invention to provide an alcohol content detecting apparatus which is substantially immune to the drawbacks of the apparatus known heretofore and which is capable of detecting an alcohol content of a liquid admixed with alcohol with high accuracy and reliability regardless of variations in the resonance frequency.

In view of the above and other objects which will become more apparent as description proceeds, there is provided according to an aspect of the present invention an apparatus for detecting an alcohol content of a liquid, which apparatus comprises a dielectric constant detecting means including a resonance circuit whose resonance frequency changes in accordance with a dielectric constant of a liquid containing alcohol, a resonance frequency detecting means for outputting a frequency signal having a same frequency as the resonance frequency of the resonance circuit of the dielectric constant detecting means, a frequency divider means for dividing the output frequency of the resonance frequency detecting means, and a frequency division ratio adjusting means for adjusting a frequency division ratio of the frequency divider means.

With the above arrangement of the alcohol content detection apparatus according to the invention, it is possible to adjust the output frequency of the frequency divider so that it bears one-to-one correspondence to the dielectric constant of the liquid regardless of apparatus-dependent variance in the resonance frequency of the resonance circuit constituting the dielectric constant detecting means by virtue of capability of adjusting the frequency division ratio of the frequency divider by the frequency division ratio adjusting means. Thus, with the apparatus according to the present invention, it is possible to detect with high accuracy the alcohol content of a liquid such as methanol content of a methanol-admixed fuel.

These and other advantages and attainments of the present invention will become apparent to those skilled in the art upon a reading of the following detailed description taken in conjunction with the drawings.

DESCRIPTION OF THE PREFERRED EMBODIMENTS

Now, the present invention will be described in detail in conjunction with preferred or exemplary embodiments thereof by reference to the drawings.

Figure 1:
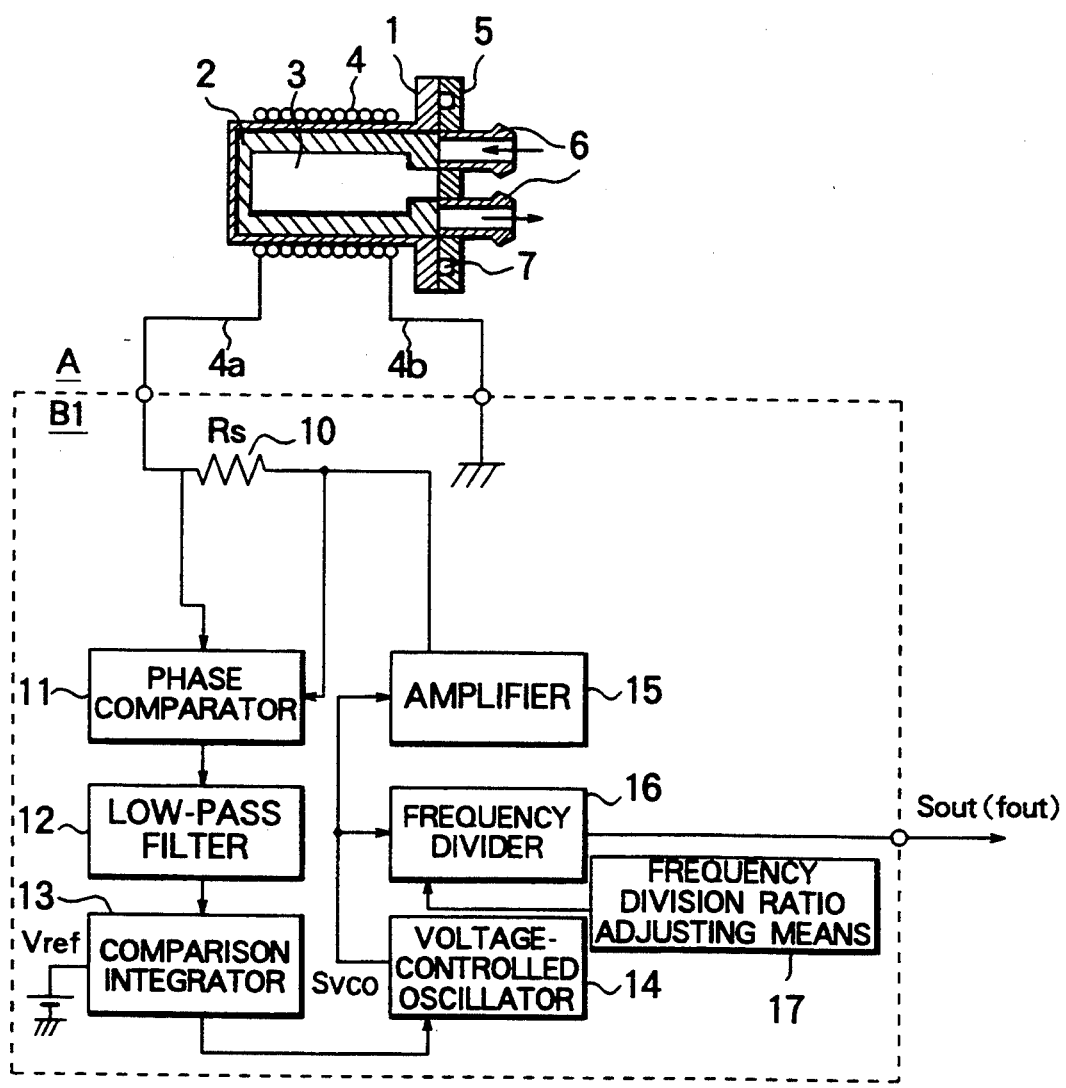
FIG. 1 is a diagram showing an alcohol content detection apparatus according to an embodiment of the present invention.

FIG. 1 shows a structure of an alcohol content detection apparatus according to an embodiment of the invention which is adapted to detect the content of methanol of a methanol-admixed fuel. In the figure, components corresponding or equivalent to those described hereinbefore by reference to FIG. 6 are denoted by like reference numerals or symbols, and repeated description thereof is omitted.

Figure 6:
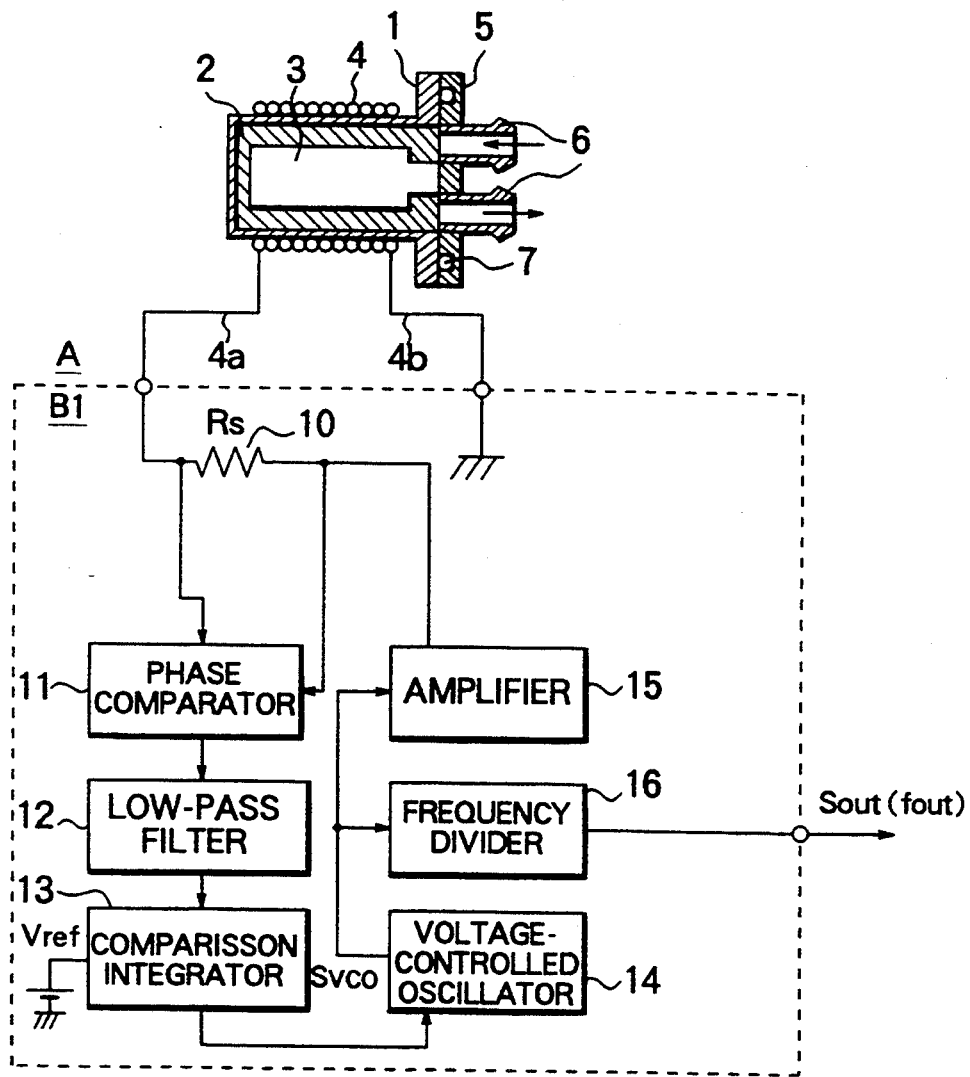
FIG. 6 is a diagram showing a structure of a hitherto known apparatus for detecting a methanol content of a methanol-admixed fuel for an internal combustion engine.
Figure 7:
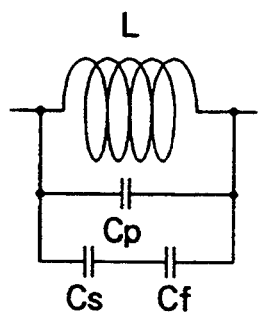
FIG. 7 shows an equivalent circuit of a sensor unit A of the apparatus shown in FIGS. 1 and 6.

The methanol content detection apparatus according to the instant embodiment differs from that shown in FIG. 6 in that a frequency division ratio adjusting circuit 17 is provided in association with the frequency divider 16 of the detection circuit unit B1 for allowing the frequency division ratio of the frequency divider 16 to be variable and thus adjustable.

Figure 2:
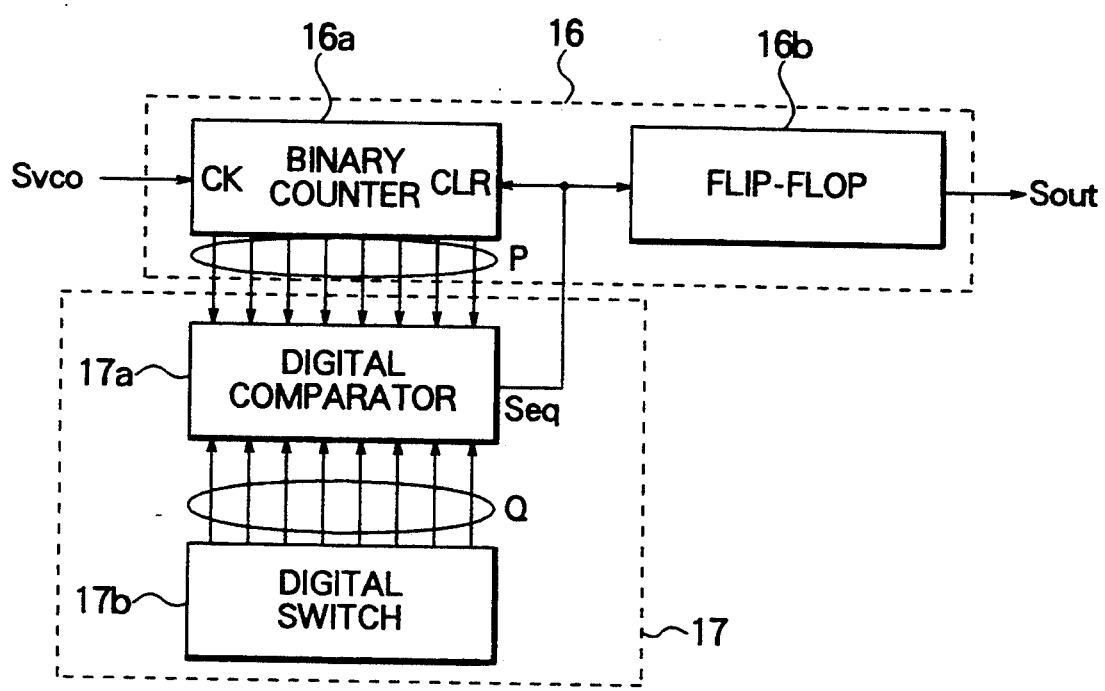
FIG. 2 is a block diagram showing a exemplary circuit configuration of a frequency divider and a frequency division ratio adjusting means.

FIG. 2 is a circuit diagram showing exemplary circuit configurations of the frequency divider 16 and the frequency division ratio adjusting circuit 17. As can be seen from the figure, the frequency divider 16 is constituted by a binary counter 16a and a flip-flop 16b. On the other hand, the frequency division ratio adjusting circuit 17 is constituted by a digital comparator 17a and a digital switch 17b.

The binary counter 16a constituting a part of the frequency divider 16 has a clock terminal CK to which the oscillation signal $S_{vco}$ outputted from the voltage-controlled oscillator 14 is applied. The binary counter 16a is adapted to be incremented in response to a leading edge (rise-up edge) or a trailing edge (falling edge) of the oscillation signal $S_{vco}$. A count output P of this counter 16a is supplied to one input terminal of the digital comparator 17a constituting a part of the frequency division ratio adjusting circuit 17. The other input terminal of the comparator 17a is supplied with a digital signal representative of a digital value Q set at the digital switch 17b.

The comparator 17a compares the input digital values P and Q to thereby output an equal signal $S_{eq}$, for example, of high or "H" level when coincidence is found between both the inputs. The equal signal $S_{eq}$ outputted from the comparator 17a is applied to a clear terminal CLR of the counter 16a and at the same time to the clock terminal CK of the flip-flop 16b. The output of the flip-flop 16b is inverted every time the equal signal $S_{eq}$ is applied to the clock terminal CK. The output signal of the flip-flop 16b is delivered as the output signal $S_{out}$ of the frequency divider 16.

With the arrangement described above, the counter 16a is incremented by the oscillation signal $S_{vco}$. Every time when the count output P of the counter 16a becomes equal to the digital signal Q set at the digital switch 17b, the counter 16a is reset with the output of the flip-flop 16b being inverted. Thus, the output signal $S_{out}$ of the frequency divider 16 has a frequency equal to a quotient resulting from division of the oscillation frequency $S_{vco}$ outputted from the voltage-controlled oscillator 14 by 2Q (where Q represents the value set at the digital switch 17B). Thus, the frequency division ratio R of the frequency divider 16 which is given by $R = 1/(2 \times Q)$ can be adjusted by means of the digital switch 17b constituting a part of the frequency division ratio adjusting circuit 17.

Figure 3:
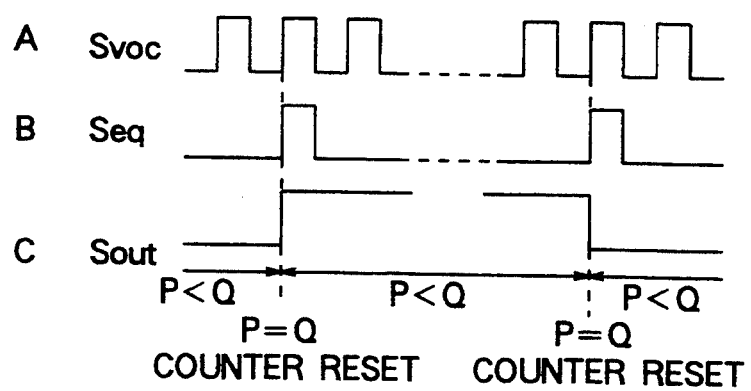
FIG. 3 is a signal waveform diagram for illustrating operation of the circuit shown in FIG. 2.

Referring to FIG. 3, there are illustrated the waveforms of the oscillation signal $S_{vco}$ of the voltage-controlled oscillator 14, the equal signal $S_{eq}$ outputted from the comparator 17b and the output signal $S_{out}$ of the frequency divider 16 at A, B and C, respectively.

Now, description will turn to the adjustment of the frequency division ratio of the frequency divider 16 by referring to FIG. 1 as well. The fuel passage 2 of the sensor unit A is filled with a predetermined fuel having a specific dielectric constant in a range, for example, of 10 to 25 or a test liquid such as isopropyl alcohol. In this state, the frequency division ratio R of the frequency divider 16 is adjusted with the aid of the frequency division ratio adjusting means 17 so that the frequency $f_{out}$ of the output signal $S_{out}$ of the frequency divider 16 assumes a reference frequency $f_{ref}$ which corresponds to the predetermined dielectric constant of the fuel or test liquid mentioned above. This adjustment can be effected by varying the digital value Q set at the digital switch 17b of the frequency division adjusting circuit 17.

At this juncture, let's represent by $f_o$ the oscillation frequency of the voltage-controlled oscillator 14 in the state in which the fuel passage 2 of the sensor unit A is filled with the predetermined fuel or test liquid mentioned above. Then, the frequency division ratio R of the frequency divider 16 can be given by the following expression $$R = INT(f_o/f_{ref} + 0.5) \quad (2)$$

In the above expression, with the addition of "0.5", it is contemplated to take into account the rounding of the quotient resulting from division of $f_o$ by $f_{ref}$ so that the frequency division ratio as obtained can be given in terms of an integer.

Thus, assuming, by way of example, that the reference frequency $f_{ref}$ is 4 kHz and that the basic frequency division ratio of the frequency divider 16 is 1/2000, the fineness of the adjustment as realized is on the order of 2 Hz (= 4000/2000), which means that sufficiently high accuracy can be ensured for the detection or measurement of the methanol or alcohol content.

Figure 4:
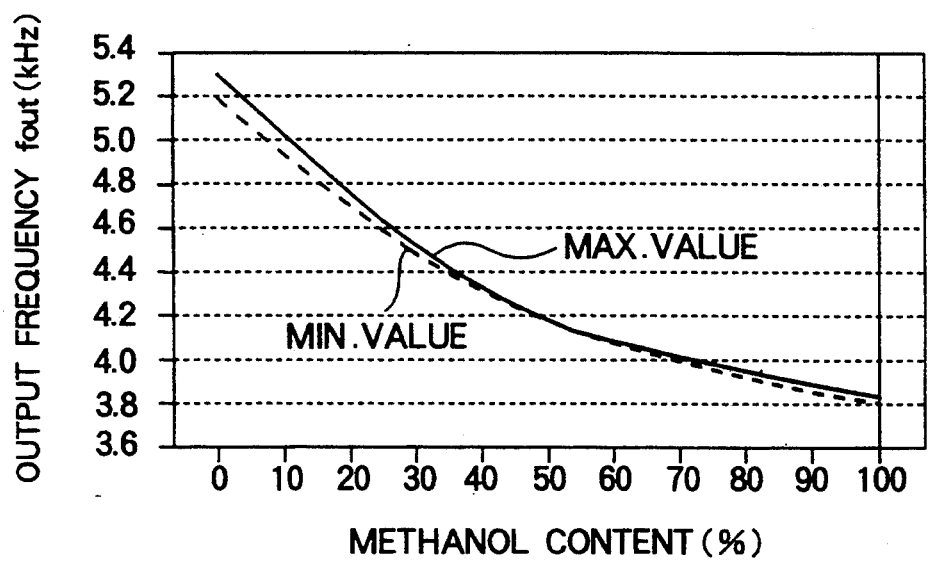
FIG. 4 is a view showing graphically output characteristics of the apparatus shown in FIG. 1.

By adjusting the frequency division ratio of the frequency divider 16 in the manner described above, the characteristic shown in FIG. 8 is modified to that illustrated in FIG. 4. More specifically, the characteristic shown in FIG. 4 is obtained by adjusting the frequency division ratio according to the teaching of the invention in the case where a test liquid containing methanol at a content of 60% is used as a reference liquid.

Figure 5:
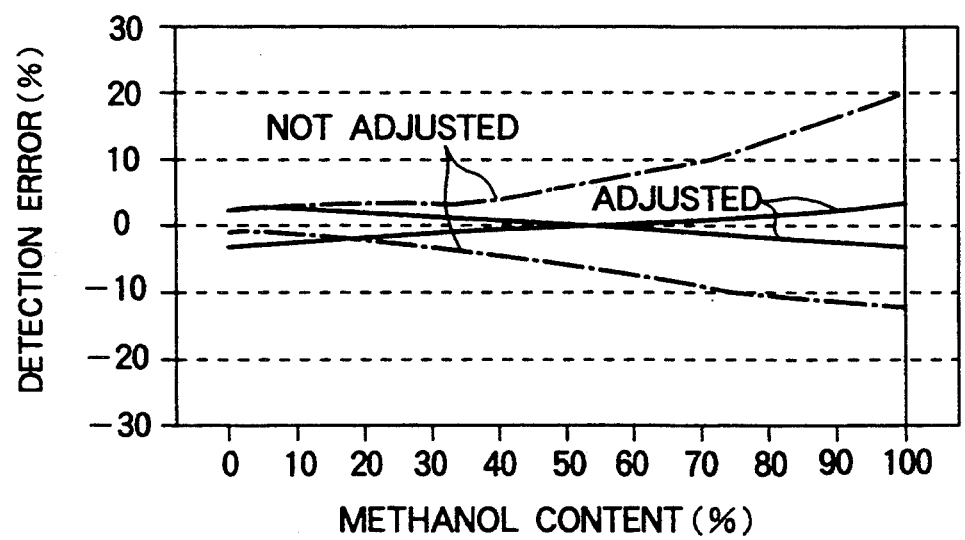
FIG. 5 is a view for graphically illustrating detection error in the apparatus shown in FIG. 1 in comparison with that of an apparatus known heretofore.
Figure 8:
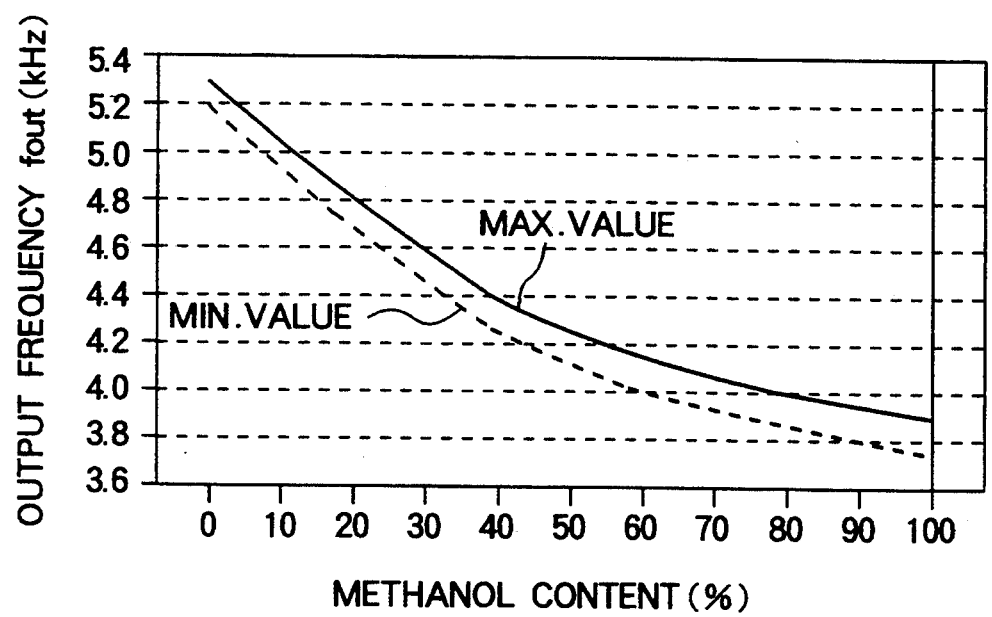
FIG. 8 is a view showing graphically an output characteristic of the apparatus known heretofore.

FIG. 5 shows errors involved in the detection of the methanol content with the characteristic shown in FIG. 4 comparatively with that of the content detection based on the characteristic illustrated in FIG. 8. As can be seen from FIG. 5, the accuracy of detection of the methanol content can remarkably be improved by virtue of the adjustability of the frequency division ratio of the frequency divider 16.

Many features and advantages of the present invention are apparent from the detailed specification and thus it is intended by the appended claims to cover all such features and advantages of the system which fall within the true spirit and scope of the invention. Further, since numerous modifications and changes will readily occur to those skilled in the art, it is not desired to limit the invention to the exact construction and operation illustrated and described. By way of example, in the case of the embodiment of the invention described above, it is assumed that the single-layer-winding coil 4 and the electrode 3 of the sensor unit A extend coaxially with each other. It should however be appreciated that such coaxial relation is not necessarily required, but it is sufficient that an electrostatic capacity due to a fuel is present between the inner surface of the single-layer-winding coil 4 and the electrode. Further, although the invention has been described in conjunction with detection of the methanol content of a methanol-admixed fuel, it should be understood that the invention is never limited to the detection of methanol content but can find application to detection of content of alcohol in a variety of liquids in more general sense. Accordingly, all suitable modifications and equivalents may be resorted to, falling within the scope of the invention.

I claim:

1. An apparatus for detecting an alcohol content of a liquid, comprising:
   dielectric constant detecting means including a resonance circuit whose resonance frequency changes in accordance with dielectric constant of a liquid containing alcohol;
   resonance frequency detecting means for outputting a frequency signal having a same frequency as the resonance frequency of said resonance circuit of said dielectric constant detecting means;
   frequency divider means for dividing the output frequency of said resonance frequency detecting means to thereby output a signal indicative of said dielectric constant on the basis of which said alcohol content can be determined; and
   frequency division ratio adjusting means for adjusting a frequency division ratio of said frequency divider means.

2. An alcohol content detecting apparatus according to claim 1,
   wherein said dielectric constant detecting means includes:
   a cylindrical tube formed of an insulation material;
   a coil of a single layer winding wound around an other cylindrical surface of said tube;
   an electrode disposed within said tube and extending substantially along the longitudinal axis of said tube; and
   a liquid flow chamber defined within said tube between said electrode and an inner cylindrical surface of said tube,
   wherein one end of said coil is connected to an input of said resonance frequency detecting means with the other end of said coil and said electrode being connected to the ground potential.

3. An alcohol content detecting apparatus according to claim 2,
   wherein said resonance frequency detecting means includes:
   a resistor having one end connected to said one end of said coil and the other end connected to an output of a voltage-controlled oscillator;
   a phase comparator for performing phase comparison between signals appearing at both ends of said resistor; and
   an integrator for integrating the output of said phase comparator;
   wherein the output of said integrator is applied to a control input terminal of said voltage-controlled oscillator so that the output frequency thereof becomes equal to a resonance frequency applied to said one end of said resistor, and wherein the output frequency of said voltage-control oscillator is divided by said frequency divider to be outputted as the signal indicative of the dielectric constant and hence the alcohol content of said liquid.

4. An alcohol content detecting apparatus according to claim 3,
   wherein said frequency divider means includes:
   a binary counter having an input terminal supplied with an oscillation signal outputted from said voltage-controlled oscillator, said counter being incremented in response to every input of said oscillation signal; and
   a flip-flop having an input terminal connected to an output terminal of said counter,
   said frequency division ratio adjusting means including:
   a digital switch at which a digital value representing a frequency division ratio is adjustably set; and
   a digital comparator for comparing the content of said counter and the digital value set at said digital switch to thereby output a coincidence signal every time when coincidence is found between said content of said counter and said digital value;
   wherein the state of said flip-flop is inverted in response to said coincidence signal, the output signal of said flip-flop being delivered as the output of said frequency divider.

* * * * *